United States Patent [19]

Hoffmann et al.

[11] 4,036,947
[45] July 19, 1977

[54] O-ALKYL-N-SUBUSTITUTED-S-HALO-PHENOXYMETHYL-DITHIOPHOS-PHORIC ACID ESTER-AMIDES

[75] Inventors: Hellmut Hoffmann, Wuppertal; Bernhard Homeyer, Opladen; Ingeborg Hammann, Cologne; Wilhelm Stendel, Wuppertal, all of Germany

[73] Assignee: Bayer Aktiengesellschaft, Leverkusen, Germany

[21] Appl. No.: 638,875

[22] Filed: Dec. 8, 1975

[30] Foreign Application Priority Data

Dec. 10, 1974 Germany .............................. 2458329

[51] Int. Cl.² .......................... A01N 9/36; C07F 9/24
[52] U.S. Cl. .................................... 424/217; 260/951
[58] Field of Search ........................ 260/951; 424/217

[56] References Cited

U.S. PATENT DOCUMENTS 3,165,545  1/1965  Blair ................................ 260/951 X
3,368,002  2/1968  Szabo et al. ........................ 260/951
3,793,407  2/1974  Stolzer et al. .................... 424/217 X Primary Examiner—Anton H. Sutto
Attorney, Agent, or Firm—Burgess, Dinklage & Sprung

[57] ABSTRACT

O-Alkyl-N-substituted-S-halophenoxymethyl-dithiophosphoric acid ester-amides of the formula

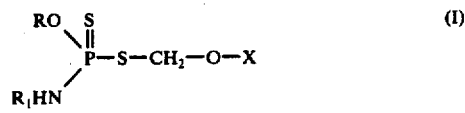

in which
R is alkyl with 1 to 4 carbon atoms,
$R_1$ is alkyl with 1 to 6 or alkenyl with 2 to 5 carbon atoms and
X is halophenyl, which possess insecticidal, acaricidal and nematocidal properties.

11 Claims, No Drawings

O-ALKYL-N-SUBUSTITUTED-S-HALOPHENOX-YMETHYL-DITHIOPHOSPHORIC ACID ESTER-AMIDES

The present invention relates to and has for its objects the provision of particular new O-alkyl-N-alkyl-or-alkenyl-S-halophenoxymethyl-dithiophosphoric acid ester-amides, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It has been disclosed in Belgian Pat. No. 544,659, British patent specification No. 1,133,511 and published Japanese Pat. No. 27,274/71 that O,O-dialkyl-S-(phenoxymethyl)-(di)-thiophosphoric acid esters, for example O,O-diethyl-S-(4-chlorophenoxymethyl)-thiolphosphoric acid ester (Compound A) and thiolthionophosphoric acid ester (Compound B), and O,O-dimethyl-S-(4-chloro-(Compound C) and 2,4-dichloro-phenoxymethyl)-thiolthionophosphoric acid ester (Compound D), have insecticidal and acaricidal properties.

The present invention provides S-(phenoxymethyl)-dithiophosphoric acid ester-amides of the general formula

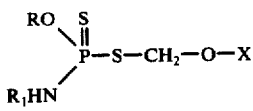

in which
R is alkyl with 1 to 4 carbon atoms,
R$_1$ is alkyl with 1 to 6 or alkenyl with 2 to 5 carbon atoms and
X is halophenyl.

Preferably, R is straight-chain or branched alkyl with 1 to 3, most preferably 1 or 2, carbon atoms, and R$_1$ is straight-chain or branched alkyl with 1 to 4, most preferably 1 to 3, carbon atoms, or straight-chain or branched alkenyl with 2 to 4, most preferably 2 or 3, carbon atoms. X is phenyl which is substituted one or more times by halogen, preferably chlorine.

Surprisingly, the S-(phenoxymethyl)-dithiophosphoric acid ester-amides according to the invention exhibit a substantially better insecticidal, acaricidal and nematocidal action than the previously known O,O-dialkylS(phenoxymethyl)-(d)thiophosphoric acid esters of analogous structure and of the same type of action. The new products are not only active against insects, mites and nematodes which damage plants but are also active, in the veterinary medicine field, against ectoparasites, for example parasitic fly larvae. They thus represent a genuine enrichment of the art.

The invention also provides a process for the production of a S-(phenoxy-methyl)-dithiophosphoric acid ester-amide of the formula (I) in which a dithiophosphoric acid ester-amide of the general formula

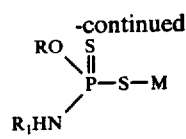

in which
R and R$_1$ have the abovementioned meanings and
M is hydrogen, an alkaline earth metal, ammonium or one equivalent of an alkali metal, is reacted with an aryl-halomethyl-ether of the formula

in which
X has the abovementioned meaning and
Hal is halogen, preferably chlorine.

The reaction may be carried out if appropriate in the presence of an acid acceptor. It may be carried out in the presence of a solvent, which term includes a mere diluent.

If, for example, the potassium salt of O-n-propyl-N-ethylthionothiolphosphoric acid ester-amide and chloromethylpentachlorophenyl-ether are used as starting materials, the course of the reaction can be represented by the following formula scheme:

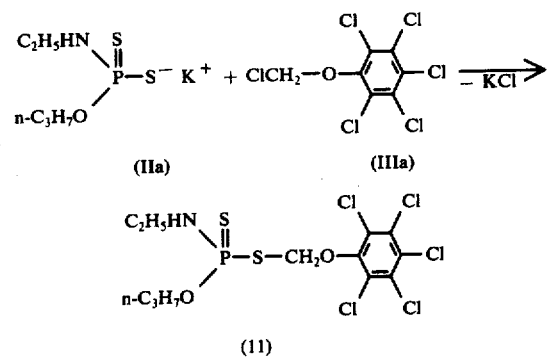

The dithiophosphoric acid ester-amides (II) are known from the literature and can be prepared according to generally known processes, even on an industrial scale, e.g. Belgian Pat. No. 770,049.

Examples of these compounds are: O-methyl-N-methyl-, O-methyl-N-ethyl-, O-methyl-N-n-propyl-, O-methyl-N-iso-propyl-, O-methyl-N-n-butyl-, O-methyl-N-iso-butyl-, O-methyl-N-tert.-butyl-, O-methyl-N-sec.-butyl-, O-methyl-N-allyl-, O-methyl-N-buten(2)yl-, O-methyl-N-buten(3)yl, O-ethyl-N-methyl-, O-ethyl-N-ethyl-, O-ethyl-N-n-propyl, O-ethyl-N-iso-propyl-, O-ethyl-N-n-butyl-, O-ethyl-N-iso-butyl-, O-ethyl-N-sec.-butyl-, O-ethyl-N-tert.-butyl-, O-ethyl-N-allyl-, O-ethyl-N-buten(2)yl-, O-ethyl-N-buten(3)yl-, O-n-propyl-N-methyl-, O-n-propyl-N-ethyl-, O-n-propyl-N-n-propyl-, O-n-propyl-N-iso-propyl-, O-n-propyl-N-n-butyl-, O-n-propyl-N-iso-butyl-, O-n-propyl-N-sec.-butyl-, O-n-propyl-N-tert.-butyl-, O-n-propyl-N-allyl-, O-n-propyl-N-buten(2)yl-, O-n-propyl-N-buten(3)yl-, O-iso-propyl-N-methyl-, O-iso-propyl-N-ethyl-, O-iso-propyl-N-n-propyl-, O-iso-propyl-N-iso-propyl-, O-iso-propyl-N-n-butyl-, O-iso-propyl-N-iso-butyl-, O-iso-propyl-sec.-butyl-, O-iso-propyl-N-tert.-butyl-, O-iso-propyl-N-allyl-, O-iso-propyl-N-buten(2)yl- and O-iso-propyl-N-buten(3)yldithiophosphoric acid ester-amide and their alkali metal salts, alkaline earth metal salts and ammonium salts.

The aryl-halomethyl-ethers (III) are known from the literature and can be prepared according to generally known methods, e.g. Organic Synthesis, Collective Volume, vol. V, page 221.

The following may be mentioned individually as examples thereof: 4-chlorophenyl-, 2,4-dichlorophenyl-, 2,4,5-trichlorophenyl-, pentachlorophenyl- and 2,4,6-trichlorophenyl-chloromethyl-ether.

The reaction according to the invention is preferably carried out in the presence of a solvent. As such, it is possible to use practically all inert organic solvents. These in particular include aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as the acid acceptor. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0 to 100, preferably at 15° to 30° C.

In general, the reaction is allowed to take place under normal pressure.

In carrying out the process, the starting materials are in general employed in equimolar ratios. An excess of one or the other component in general produces no significant advantages. The reaction is preferably carried out in one of the stated solvents, at the stated temperatures. In most cases, the phosphoric acid component is employed in the form of a salt. After a reaction time of from one to several hours, the reaction mixture may be poured into water and extracted by shaking with an organic solvent, for example methylene chloride, and the organic phase may be worked up in the usual manner by washing, drying and distilling off the solvent.

The new compounds are obtained in the form of oils which in most cases cannot be distilled without decomposition, but can be freed from the last volatile constituents by so-called "slight distillation", that is to say by prolonged heating under reduced pressure to moderately elevated temperatures, and they may be purified in this way. They are characterized by the refractive index.

As already mentioned, the S-(phenoxy-methyl)-dithiophosphoric acid ester-amides according to the invention are distinguished by an excellent insecticidal, acaricidal and nematocidal activity. They are not only active against plant pests, hygiene pests and pests of stored products, but also, in the veterinary medicine field, against animal parasites (ectoparasites), such as parasitic fly larvae. They couple a low phytotoxicity with a good action against both sucking and biting insects and mites.

For this reason, the compounds according to the invention can be employed successfully in plant protection and as pesticides in the hygiene field, the field of protection of stored products and the veterinary field.

The active compounds according to the invention are well tolerated by plants and have a favorable level of toxicity to warm-blooded animals, and can be used for combating all or individual, including the pre-embryonic, normally sensitive and resistant stages of development of arthropods and nematodes, where these are known as pests or pathogens of plant diseases in agriculture, in forestry, in the protection of stored products and in the protection of materials, as well as in hygiene.

The economically important pests in agriculture and forestry, as well as pests of stored products, material pests and hygiene pests, include: from the order of the Isopoda, for example *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and Scutigera spec.; from the order of the Symphyla, for exampla, *Scutigerella immaculata;* from the order of the Arachnida, for example, *Scorpio maurus* and *Latrodectus mactans;* from the order of the Acarina, for example *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei, Tarsonemus* spec. *Bryobia praetiosa, Panonychus citri, Panonychus ulmi, Tetranychus telarius, Tetranychus tumidus* and *Tetranychus urticae;* from the order of the Thysanura, for example *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus,* Gryllotalpa spec., *Locusta migrotoria migratorioides, Melanoplus differentialis* and *Schistocerca gregaria;* from the order of the Dermaptera, for example, *Forficula auricularia;* from the order of the Isoptera, for example, Reticulitermes spec.; from the order of the Anoplura, for example, *Phylloxera vastatrix,* Pemphigus spec. and *Pediculus humanus corporis;* from the order of the Thysanoptera, for example *Hercinothrips femoralis* and *Thrips tabaci;* from the order of the Heteroptera, for example, Eurygaster spec., *Dysdercus intermedius, Piesma quadrata, Cimex lectularius, Rhodnius prolixus* and Triatoma spec.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi,* Empoasca spec., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spec. and Psylla spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *Bucculatrix thurberiella, Phyllocnistis citrella,* Agrotis spec., Euxoa spec., Feltia spec., *Earias insulana,* Heliothis spec., *Laphygma exigua, Mamestra brassicae, Panolis flammea, Prodenia litura,* Spodoptera spec., *Trichoplusia ni, Carpocapsa pomonella,* Pieris spec., Cailo spec., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spec., *Psylliodes chrysocephala, Epilachna varivestis,* Atomaria spec., Oryzaephilus surinamensis, Anthonomus spec., Sitophilus spec., *Otiorrhynchus sulcatus, Cosmopolites sordidus, Ceuthorrhynchus assimilis, Hypera postica,* Dermestis spec., Trogoderma spec. Anthrenus spec., Attagenus spec., Lyctus spec., *Meligethes aeneus,* Ptinus spec., *Niptus holoeucus, Gibbium psylloides,* Tribolium spec., *Tenebrio molitor,* Agriotes spec., Conoderus spec., *Melolontha melolontha, Amphimallus solstitialis* and *Costelytra zealandica;* from the order of the Hymenoptera, for example, Diprion spec., Hoplocampa spec., Lasius spec., *Monomorium pharaonis* and Vespa spec.; from the order of the Diptera, for example, Aedes spec., Anopheles spec., Culex spec., *Drosophila melanogaster, Musca domestica,* Fannia spec., *Stomoxys calcitrans,* Hypoderma spec., *Bibio hortulanus, Oscinella frit,* Phorbia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example, *Xenopsylla cheopis.*

The active compounds according to the invention couple a low toxicity to warm-blooded animals with powerful nematocidal properties and can therefore be used to combat nematodes, especially phytopathogenic nematodes. These essentially include leaf nematodes (Arphelenchoides), such as the chrysanthemum eelworm (*A. ritzemabosi*), the leaf-blotch eelworm (*A. fragariae*) and the rice eelworm (*A. oryzae*); stem nematodes (Ditylenchus), such as the stem eelworm (*D. Dipsaci*); root-knot nematodes (Meloidogyne), such as *M. arenaria* and *M. incognita;* cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

When used against hygiene pests and pests of stored products, the active compounds are distinguished by an excellent residual action on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above.

tion are illustrated, without limitation, by the following examples:

EXAMPLE 1

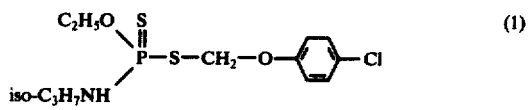

18 g (0.1 mole) of chloromethyl-4-chlorophenyl-ether were added to 25 g (0.1 mole) of the potassium salt of O-ethyl-N-iso-propylthionothiolphosphoric acid esteramide in 200 ml of acetonitrile. The reaction was slightly exothermic. The reaction mixture was left to stand overnight while being stirred and was then poured into water and extracted by shaking with methylene chloride. The phases were separated, the organic phase was washed and dried and the solvent was distilled off under reduced pressure. The residue was subjected to "slight distillation" and 26 g (76% of theory) of O-ethyl-S-(4-chlorophenoxymethyl)-N-iso-propylthionothiolphosphoric acid esteramide of refractive index $N_D^{25}$: 1.5680 were obtained.

The following compounds were prepared analogously:

Table 1

| Compound No. | Structure | Refractive index: | Yield (% of theory) |
|---|---|---|---|
| 2 | C₂H₅O\P(=S)(-S-CH₂-O-C₆H₄-Cl)/CH₂=CH-CH₂-NH | $n_D^{22}$: 1.5810 | 86 |
| 3 | C₂H₅O\P(=S)(-S-CH₂-O-C₆H₄-Cl)/CH₃-NH | $n_D^{22}$: 1.5900 | 87 |
| 4 | C₂H₅O\P(=S)(-S-CH₂-O-C₆H₃Cl₂)/CH₂=CH-CH₂-NH | $n_D^{22}$: 1.5880 | 81 |
| 5 | C₂H₅O\P(=S)(-S-CH₂-O-C₆H₃Cl₂)/iso-C₃H₇-NH | $n_D^{22}$: 1.5775 | 72 |
| 6 | C₂H₅O\P(=S)(-S-CH₂-O-C₆H₃Cl₂)/CH₃-NH | $n_D^{22}$: 1.5970 | 87 |

The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present inven- Other compounds which can be similarly prepared include:

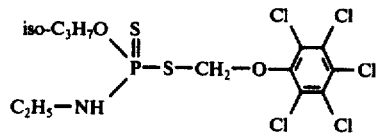

(7)

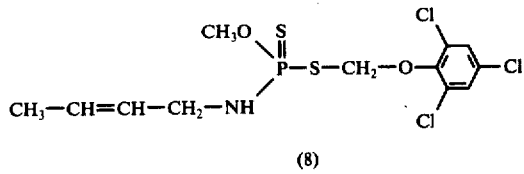

(8)

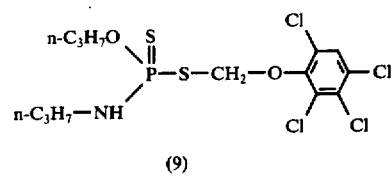

(9)

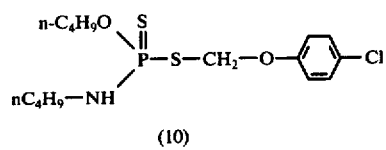

(10)

and the like.

EXAMPLE 2

Critical concentration test
Test nematode: Meloidogyne incognita
Solvent: 3 parts by weight of acetone
Emulsifier: 1 part by weight of alkylarly polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm. was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following table:

Table 2

Critical concentration test/nematicides
(Meloidogyne incognita)

| Active compound | Degree of destruction in % at an active compound concentration of 5 ppm |
|---|---|
| 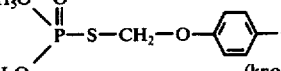 (known) | 0 |
| 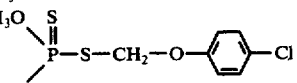 (known) | 0 |
|  (known) | 0 |
|  (known) | 0 |
| 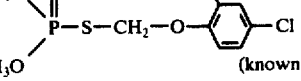 (3) | 100 |
| 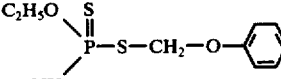 (1) | 100 |
| 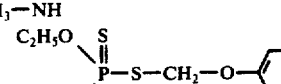 (5) | 100 |
| (6) | 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (Phaseolus vulgaris), which had a height of approximately 10-30 cm, were sprayed with the preparation of the active compound until dripping wet. These bean plants were heavily infested with the common or two-spotted spider mite (Tetranychus urticae) in all stages of development.

After the specified periods of time, the degree of destruction was determined as a percentage; 100% means that all the spider mites were killed whereas 0% means that none of the spider mites were killed.

The active compounds, the concentrations of the active compounds, the evaluation times and the results can be seen from the following table:

Table 3

(Tetranychus test)

| Active compound | Active compound concentration in % | Degree of destruction in % after 8 days |
|---|---|---|
| $(CH_3O)_2\overset{\overset{S}{\|}}{P}-S-CH_2-O-\bigcirc\text{-Cl, Cl}$ (known) (D) | 0.1 | 0 |
| $\underset{CH_3-NH}{\overset{C_2H_5O}{\diagdown}}\overset{\overset{S}{\|}}{P}-S-CH_2-O-\bigcirc\text{-Cl, Cl}$ (3) | 0.1 | 98 |
| $\underset{CH_3-NH}{\overset{C_2H_5O}{\diagdown}}\overset{\overset{S}{\|}}{P}-S-CH_2-O-\bigcirc\text{-Cl, Cl}$ (6) | 0.1 | 98 |
| $\underset{iso-C_3H_7-NH}{\overset{C_2H_5O}{\diagdown}}\overset{\overset{S}{\|}}{P}-S-CH_2-O-\bigcirc\text{-Cl}$ (1) | 0.1 | 98 |
| $\underset{iso-C_3H_7-NH}{\overset{C_2H_5O}{\diagdown}}\overset{\overset{S}{\|}}{P}-S-CH_2-O-\bigcirc\text{-Cl, Cl}$ (5) | 0.1 | 98 |
| $\underset{CH_2=CH-CH_2-NH}{\overset{C_2H_5O}{\diagdown}}\overset{\overset{S}{\|}}{P}-S-CH_2-O-\bigcirc\text{-Cl, Cl}$ (4) | 0.1 | 90 |

EXAMPLE 4

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 4

(Myzus test)

| Active compound | Active compound concentration in % | Degree of destruction in % after 1 day |
|---|---|---|
| $(C_2H_5O)_2\overset{\overset{S}{\|}}{P}-S-CH_2-O-\bigcirc\text{-Cl}$ (known) (B) | 0.1<br>0.01<br>0.001 | 100<br>50<br>0 |
| $\underset{iso-C_3H_7-NH}{\overset{C_2H_5O}{\diagdown}}\overset{\overset{S}{\|}}{P}-S-CH_2-O-\bigcirc\text{-Cl}$ (1) | 0.1<br>0.01<br>0.001 | 100<br>100<br>40 |

EXAMPLE 5

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae had been killed whereas 0% means that none of the beetle larvae had been killed.

gree of destruction in % was determined. 100% means that all larvae had been killed and 0% means that no larvae had been killed.

The active compounds investigated, the concentrations of the active compounds used and the results obtained can be seen from Table 6 which follows:

Table 6

| Active compound | (Test with parasitic fly larvae / lucilia cuprina, resistant) Active compound concentration in ppm | Degree of destruction in % |
|---|---|---|
| C₂H₅O\\P(=S)(NHCH₃)—S—CH₂—O—(3-Cl,4-Cl-phenyl) (6) | 100<br>30<br>10<br>3 | 100<br>100<br>100<br>100 |
| C₂H₅O\\P(=S)(NH-iso-C₃H₇)—S—CH₂—O—(3-Cl,4-Cl-phenyl) (5) | 100<br>30<br>10 | 100<br>100<br>100 |
| (CH₃O)₂P(=S)—S—CH₂—O—(3-Cl,4-Cl-phenyl) (known) (D) | 100<br>30<br>10 | 100<br>100<br>0 |

The active compounds, the concentrations of the active compounds, the evaluation times and the results can be seen from the following table:

Table 5

| Active compound | (Phaedon larvae test) Active compound concentration in % | Degree of destruction in % after 3 days |
|---|---|---|
| (C₂H₅O)₂P(=O)—S—CH₂—O—(4-Cl-phenyl) (known) (A) | 0.1<br>0.01 | 100<br>0 |
| C₂H₅O\\P(=S)(NHCH₃)—S—CH₂—O—(3-Cl,4-Cl-phenyl) (6) | 0.1<br>0.01 | 100<br>100 |
| C₂H₅O\\P(=S)(NH-iso-C₃H₇)—S—CH₂—O—(3-Cl,4-Cl-phenyl) (5) | 0.1<br>0.01 | 100<br>100 |

It will be appreciated that the instant specification and examples are set forth by way of illustration and not limitation, and that various modifications and changes may be made without departing from the spirit and scope of the present invention.

What is claimed is:

1. An O-alkyl-N-substituted-S-halopenoxymethyldithiophosphoric acid ester-amide of the formula

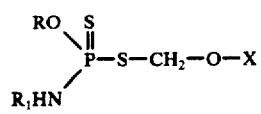

in which
R is alkyl with 1 to 4 carbon atoms,
R₁ is alkyl with 1 to 6 or alkenyl with 2 to 5 carbon atoms and

EXAMPLE 6

Test with parasitic fly larvae

Solvent: 35 parts by weight of ethylene polyglycol monomethyl ether 35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the de- X is chlorophenyl.

2. A compound according to claim 1 in which R is alkyl with 1 to 3 carbon atoms, $R_1$ is alkyl or alkenyl with up to 4 carbon atoms.

3. The compound according to claim 1, wherein such compound is O-ethyl-S-(4-chlorophenoxymethyl)-N-iso-propylthionothiolphosphoric acid ester-amide of the formula

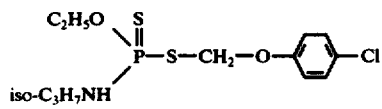

4. The compound according to claim 1 wherein such compound is O-ethyl-S-(4-chlorophenoxymethyl)-N-allylthionothiolphosphoric acid ester-amide of the formula

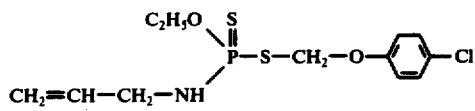

5. The compound according to claim 1 wherein such compound is O-ethyl-S-(4-chlorophenoxymethyl)-N-methylthionothiolphosphoric acid ester-amide of the formula

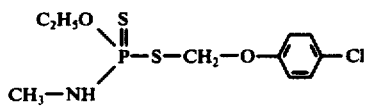

6. The compound according to claim 1 wherein such compound is O-ethyl-S-(2,4-dichlorophenoxymethyl)-N-allylthionothiolphosphoric acid ester-amide of the formula

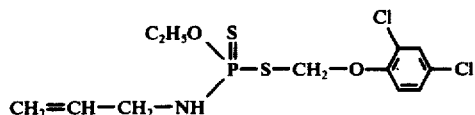

7. The compound according to claim 1 wherein such compound is O-ethyl-S-(2,4-dichlorophenoxymethyl)-N-iso-propylthionothiolphosphoric acid ester-amide of the formula

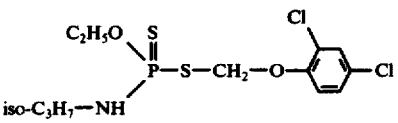

8. The compound according to claim 1 wherein such compound is O-ethyl-S-(2,4-dichlorophenoxymethyl)-N-methylthionothiolphosphoric acid ester-amide of the formula

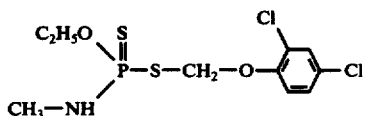

9. An insecticidal, acaricidal or nematocidal composition containing as active ingredients an insecticidally, acaricidally or nematocidally effective amount of a compound according to claim 1 in admixture with a diluent.

10. A method of combating insect, acarid or nematode pests which comprises applying to the pests or a habitat thereof an insecticidally, acaricidally or nematocidally effective amount of a compound according to claim 1.

11. The method according to claim 10 in which said compound is
O-ethyl-S-(4-chlorophenoxymethyl)-N-iso-propylthionothiolphosphoric acid ester-amide,
O-ethyl-S-(4-chlorophenoxymethyl)-N-allylthionothiolphosphoric acid ester amide,
O-ethyl-S-(4-chlorophenoxymethyl)-N-methylthionothiolphosphoric acid ester-amide,
O-ethyl-S-(2,4-dichlorophenoxymethy)-N-allylthionothiolphosphoric acid ester-amide,
O-ethyl-S-(2,4-dichlorophenoxymethyl)-N-iso-propylthionothiolphosphoric acid ester-amide or
O-ethyl-S-(2,4-dichlorophenoxymethyl)-N-methylthionothiolphosphoric acid ester-amide.

* * * * *